(12) United States Patent
Hsieh et al.

(10) Patent No.: US 12,082,774 B2
(45) Date of Patent: Sep. 10, 2024

(54) SYSTEM AND METHOD FOR ASSISTING ENDOSCOPE TRACKING

(71) Applicant: METAL INDUSTRIES RESEARCH & DEVELOPMENT CENTRE, Kaohsiung (TW)

(72) Inventors: Yu-Sung Hsieh, Tainan (TW); Bing-Feng Huang, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 491 days.

(21) Appl. No.: 17/644,782

(22) Filed: Dec. 16, 2021

(65) Prior Publication Data
US 2023/0190075 A1 Jun. 22, 2023

(51) Int. Cl.
*A61B 1/00* (2006.01)
*A61B 5/06* (2006.01)
*A61B 34/20* (2016.01)

(52) U.S. Cl.
CPC .......... *A61B 1/00055* (2013.01); *A61B 5/067* (2013.01); *A61B 2034/2048* (2016.02); *A61B 2562/0219* (2013.01)

(58) Field of Classification Search
CPC ............... A61B 1/00055; A61B 5/067; A61B 2034/2048; A61B 2562/0219; A61B 2034/2046; A61B 1/00006; A61B 1/00097
See application file for complete search history.

(56) References Cited

U.S. PATENT DOCUMENTS 7,623,900 B2 11/2009 Graham et al.
2003/0152897 A1 8/2003 Geiger

FOREIGN PATENT DOCUMENTS

TW I432168 B 4/2014

*Primary Examiner* — Alexei Bykhovski
(74) *Attorney, Agent, or Firm* — CKC & Partners Co., LLC

(57) ABSTRACT

A system for assisting endoscope tracking used to track a travel path of an endoscope probe within an organ includes three position sensors and three distance sensors which are surrounding an endoscope probe, and a computing device. The said three position sensors respectively sense a first coordinate, a second coordinate and a third coordinate relative to a navigation origin. The said three distance sensors respectively sense a first distance, a second distance and a third distance apart from an inner wall of the organ. The computing device obtains a position coordinate of the endoscope probe relative to the navigation origin according to the first coordinate, the second coordinate and the third coordinate. The computing device further determines whether to send a warning message according to the first distance, the second distance and the third distance.

16 Claims, 5 Drawing Sheets

SYSTEM AND METHOD FOR ASSISTING ENDOSCOPE TRACKING

BACKGROUND

Field of Invention

The present disclosure relates to a system and a method for assisting endoscope tracking. More particularly, the present invention relates to an endoscope surgical guide system and an endoscope surgical guide method for assisting endoscope tracking.

Description of Related Art

During the operation of endoscope surgery, if the length of the endoscope tube is too long, it will be difficult to manipulate, and the endoscope tube bends around within the curved intestine. Therefore, the doctors are difficult to diagnose the small intestine disease. In addition, when the doctors are operating the endoscope probe and facing the situation that the endoscope image is not clear or the organ of the intestine is complicated, the endoscope image can merely provide surgical guidance with a limited angle of view and cannot provide the doctors with the accurately travelling direction for operating the endoscope probe. Thus, if the control of the forward or backward travelling direction of the endoscope probe is deviated, the inner wall of the organ of the intestine may be collided by the endoscope probe. The said collision causes pain in the patient and may increase the risk of penetration of the inner wall of the organ of the intestine, and in the worst case, the said collision may cause the patient's death.

In recent years, the technology of various image processing methods for optimizing the intestine image quality to facilitate the doctors to operate the endoscope probe is quite popular. However, the said technology is limited due to plural factors, such as the hardware specifications of the image capturing elements, plural turning points within the intestine, the frequent spread of creases between the cavity and the inner wall of the organ of the intestine, etc., and therefore the said technology of intestine image processing methods still faces plural difficulties.

SUMMARY

The present invention provides a system for assisting endoscope tracking used to track a travel path of an endoscope probe within an organ includes: a first position sensor, a second position sensor, a third position sensor, a first distance sensor, a second distance sensor, a third distance sensor and a computing device. The first position sensor is configured to sense a first coordinate of the first position sensor relative to a navigation origin. The second position sensor is configured to sense a second coordinate of the second position sensor relative to the navigation origin. The third position sensor is configured to sense a third coordinate of the third position sensor relative to the navigation origin. The first position sensor, the second position sensor and the third position sensor are surrounding the endoscope probe. The first distance sensor is adjacent to the first position sensor and is configured to sense a first distance between the first distance sensor and an inner wall of the organ. The second distance sensor is adjacent to the second position sensor and is configured to sense a second distance between the second distance sensor and the inner wall of the organ. The third distance sensor is adjacent to the third position sensor and is configured to sense a third distance between the third distance sensor and the inner wall of the organ. The computing device is configured to obtain a position coordinate of the endoscope probe relative to the navigation origin according to the first coordinate, the second coordinate and the third coordinate. The computing device is further configured to determine whether to send a warning message according to the first distance, the second distance and the third distance.

In accordance with one or more embodiments of the invention, each of the first position sensor, the second position sensor and the third position sensor is a MEMS inertial sensing device composed of a gyroscope and an accelerometer.

In accordance with one or more embodiments of the invention, each of the first distance sensor, the second distance sensor and the third distance sensor is an infrared distance sensor. A detectable range of the infrared distance sensor is 0 to 6 cm.

In accordance with one or more embodiments of the invention, the position coordinate is an average value of the first coordinate, the second coordinate and the third coordinate. The computing device draws the travel path of the endoscope probe within the organ according to the position coordinate.

In accordance with one or more embodiments of the invention, when one of the first distance, the second distance and the third distance is less than a distance threshold, the computing device sends the warning message.

In accordance with one or more embodiments of the invention, the system further includes a first position error correcting filter, a second position error correcting filter and a third position error correcting filter. The first position error correcting filter is configured to correct the first coordinate sensed by the first position sensor. The second position error correcting filter is configured to correct the second coordinate sensed by the second position sensor. The third position error correcting filter is configured to correct the third coordinate sensed by the third position sensor.

In accordance with one or more embodiments of the invention, each of the first position error correcting filter, the second position error correcting filter and the third position error correcting filter is a complimentary filter.

In accordance with one or more embodiments of the invention, the system further includes a storage device configured to store the position coordinate corresponding to a lesion and an image corresponding to the lesion. The image is captured by the endoscope probe.

The present invention further provides a method for assisting endoscope tracking used to track a travel path of an endoscope probe within an organ includes: sensing a first coordinate of a first position sensor relative to a navigation origin; sensing a second coordinate of a second position sensor relative to the navigation origin; sensing a third coordinate of a third position sensor relative to the navigation origin, in which the first position sensor, the second position sensor and the third position sensor are surrounding the endoscope probe; sensing a first distance between a first distance sensor and an inner wall of the organ, in which the first distance sensor is adjacent to the first position sensor; sensing a second distance between a second distance sensor and the inner wall of the organ, in which the second distance sensor is adjacent to the second position sensor; sensing a third distance between the third distance sensor and the inner wall of the organ, in which the third distance sensor is adjacent to the third position sensor; obtaining a position coordinate of the endoscope probe relative to the navigation origin according to the first coordinate, the second coordinate and the third coordinate; and determining whether to send a warning message according to the first distance, the second distance and the third distance.

In accordance with one or more embodiments of the invention, each of the first position sensor, the second position sensor and the third position sensor is a MEMS inertial sensing device composed of a gyroscope and an accelerometer.

In accordance with one or more embodiments of the invention, each of the first distance sensor, the second distance sensor and the third distance sensor is an infrared distance sensor. A detectable range of the infrared distance sensor is 0 to 6 cm.

In accordance with one or more embodiments of the invention, the method further includes: drawing the travel path of the endoscope probe within the organ according to the position coordinate. The position coordinate is an average value of the first coordinate, the second coordinate and the third coordinate.

In accordance with one or more embodiments of the invention, the method further includes: sending the warning message when one of the first distance, the second distance and the third distance is less than a distance threshold.

In accordance with one or more embodiments of the invention, the method further includes: correcting the first coordinate sensed by the first position sensor by a first position error correcting filter; correcting the second coordinate sensed by the second position sensor by a second position error correcting filter; and correcting the third coordinate sensed by the third position sensor by a third position error correcting filter.

In accordance with one or more embodiments of the invention, each of the first position error correcting filter, the second position error correcting filter and the third position error correcting filter is a complimentary filter.

In accordance with one or more embodiments of the invention, the method further includes: storing the position coordinate corresponding to a lesion and an image corresponding to the lesion. The image is captured by the endoscope probe.

In order to let above mention of the present invention and other objects, features, advantages, and embodiments of the present invention to be more easily understood, the description of the accompanying drawing as follows.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Specific embodiments of the present invention are further described in detail below with reference to the accompanying drawings, however, the embodiments described are not intended to limit the present invention and it is not intended for the description of operation to limit the order of implementation. The using of "first", "second", "third", etc. in the specification should be understood for identify units or data described by the same terminology, but are not referred to particular order or sequence.

Figure 1:
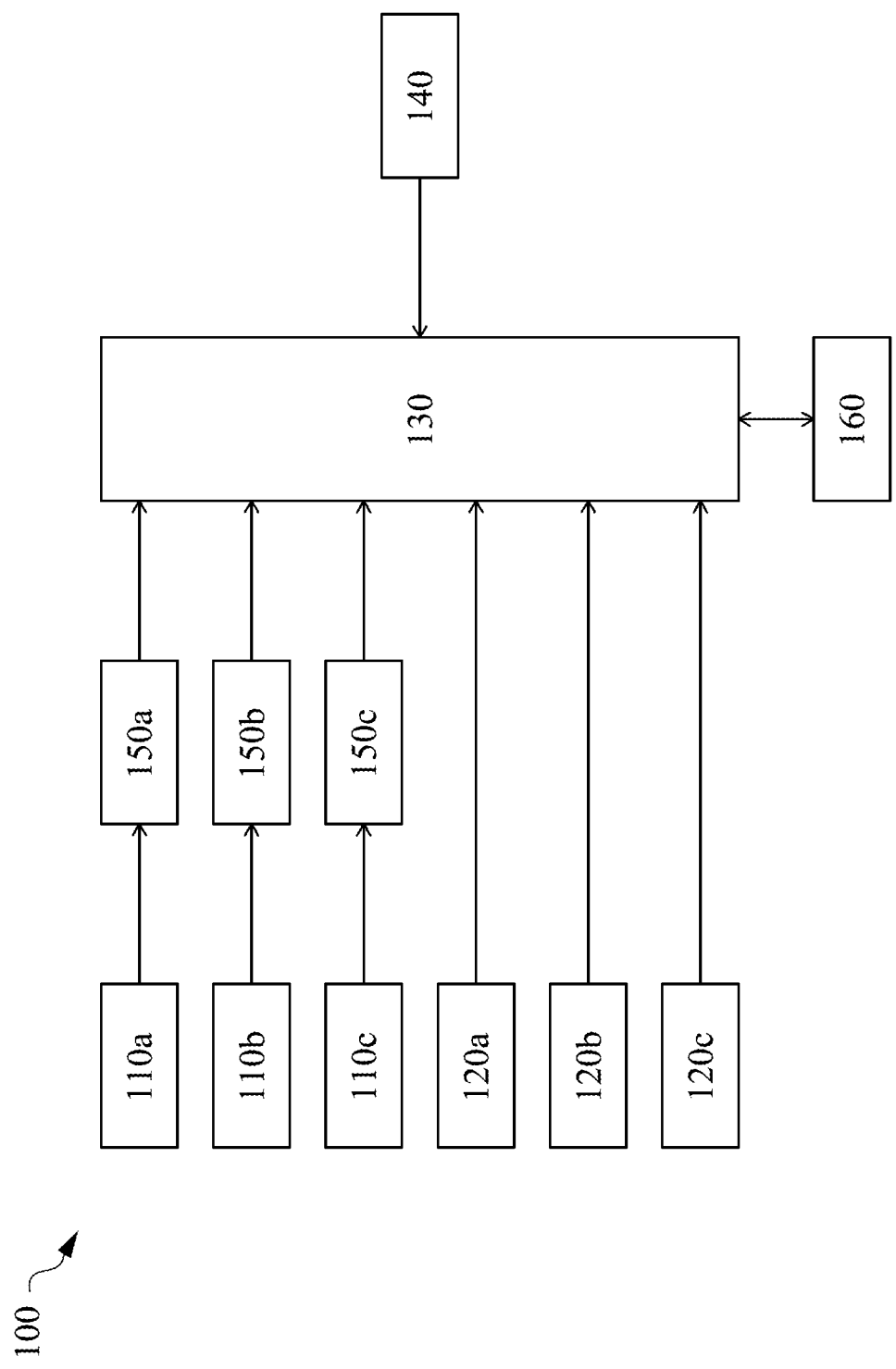
FIG. 1 illustrates a block diagram of a system for assisting endoscope tracking according to some embodiments of the present invention.
Figure 2:
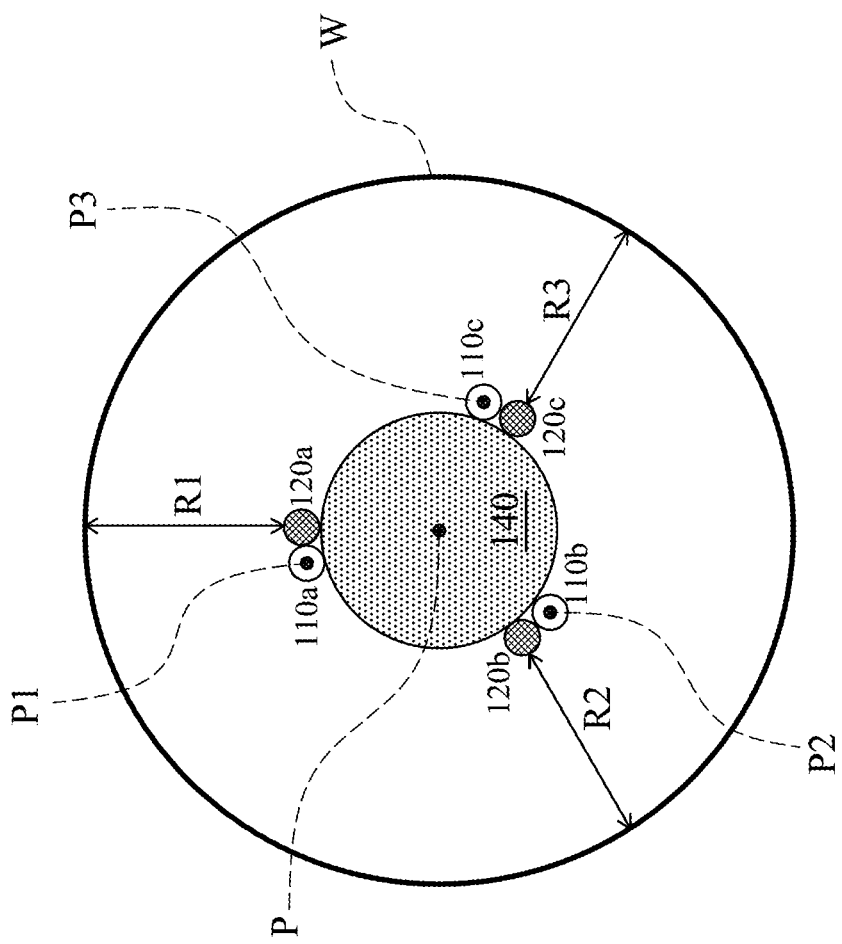
FIG. 2 illustrates a top view of the component arrangement of the system for assisting endoscope tracking according to some embodiments of the present invention.

FIG. 1 illustrates a block diagram of a system 100 for assisting endoscope tracking according to some embodiments of the present invention. FIG. 2 illustrates a top view of the component arrangement of the system 100 for assisting endoscope tracking according to some embodiments of the present invention. The system 100 for assisting endoscope tracking includes: a first position sensor 110a, a second position sensor 110b, a third position sensor 110c, a first distance sensor 120a, a second distance sensor 120b, a third distance sensor 120c and a computing device 130.

As shown in FIG. 2, the first position sensor 110a, the second position sensor 110b and the third position sensor 110c are surrounding the endoscope probe 140. The first distance sensor 120a is adjacent to the first position sensor 110a. The second distance sensor 120b is adjacent to the second position sensor 110b. The third distance sensor 120c is adjacent to the third position sensor 110c.

Specifically, in order to prevent the position sensors (110a, 110b, 110c) and the distance sensors (120a, 120b, 120c) from shielding the endoscope probe 140 for taking the endoscope image, the position sensors (110a, 110b, 110c) and the distance sensors (120a, 120b, 120c) are arranged around the endoscope probe 140. For example, the endoscope probe 140 is in the shape of a cylinder, and the camera part of the endoscope probe 140 is located on the top of the cylinder. The position sensors (110a, 110b, 110c) and the distance sensors (120a, 120b, 120c) are installed on the side surface of the said cylinder.

As shown in FIG. 2, the first position sensor 110a, the second position sensor 110b and the third position sensor 110c are equidistantly arranged around the endoscope probe 140. The first distance sensor 120a, the second distance sensor 120b and the third distance sensor 120c are equidistantly arranged around the endoscope probe 140.

In some embodiments of the present invention, at the beginning of the endoscope surgery, the system 100 for assisting endoscope tracking firstly defines a starting point of the endoscope probe 140 entering the patient's body as the navigation origin (not shown). The first position sensor 110a is used for sensing a first coordinate P1 of the first position sensor 110a relative to the navigation origin. The second position sensor 110b is used for sensing a second coordinate P2 of the second position sensor 110b relative to the navigation origin. The third position sensor 110c is used for sensing a third coordinate P3 of the third position sensor 110c relative to the navigation origin.

In some embodiments of the present invention, each of the first position sensor 110a, the second position sensor 110b and the third position sensor 110c is a MEMS (Micro Electro Mechanical Systems) inertial sensing device (or called an inertial measurement unit (IMU)) composed of a gyroscope and an accelerometer. The accelerometer provides the acceleration information, such that the velocity information can be obtained by integrating the acceleration information, and then the displacement information can be obtained by integrating the velocity information. The formula is shown as follows:

$$a = \frac{dV}{dt} = \frac{d^2S}{dt^2} \quad (1)$$

$$V = V_0 + \int_0^T a\,dt \quad (2)$$

$$S = S_0 + \int_0^T V\,dt = S_0 + V_0 + \int\int_0^T a\,dt^2 \quad (3)$$

"a" is the acceleration, "V" is velocity, "$V_0$" is initial velocity, "t" is time, "S" is displacement, and "$S_0$" is initial displacement. The gyroscope provides the angular velocity information, such that the angular displacement (angle variation) information can be obtained by integrating the angular velocity information, and then the Euler angle can be obtained according to the initial attitude and the angular displacement information, and then the azimuth angle is calculated through the Euler angle, so as to obtain the angle information and the direction information. Specifically, the present invention utilizes the MEMS inertial sensing device composed of a gyroscope and an accelerometer to obtain the acceleration information and the angular velocity information, thereby calculating the Euler angle and the azimuth angle, and the position information is calculated through time integration manner. The calculation process for obtaining position information (i.e., the coordinate P1, P2, or P3) by using the gyroscope and accelerometer should be a known technology in the relevant field, and will not be discussed and explained here.

The first distance sensor 120a is used for sensing a first distance R1 between the first distance sensor 120a and an inner wall W of the organ. The second distance sensor 120b is used for sensing a second distance R2 between the second distance sensor 120b and the inner wall W of the organ. The third distance sensor 120c is used for sensing a third distance R3 between the third distance sensor 120c and the inner wall W of the organ.

In some embodiments of the present invention, each of the first distance sensor 120a, the second distance sensor 120b and the third distance sensor 120c is an infrared distance sensor. Since the diameter of the small intestine is about 2 cm and the diameter of the large intestine is about 5 to 6 cm, the detectable range of the infrared distance sensor of the present invention is set as 0 to 6 cm.

As shown in FIG. 1, the system 100 for assisting endoscope tracking further includes: a first position error correcting filter 150a, a second position error correcting filter 150b and a third position error correcting filter 150c. The first position error correcting filter 150a is communicatively connected to the first position sensor 110a to correct the first coordinate P1 sensed by the first position sensor 110a. The second position error correcting filter 150b is communicatively connected to the second position sensor 110b to correct the second coordinate P2 sensed by the second position sensor 110b. The third position error correcting filter 150c is communicatively connected to the third position sensor 110c to correct the third coordinate P3 sensed by the third position sensor 110c.

Specifically, since the said coordinates (P1, P2, P3) sensed by the position sensors (110a, 110b, 110c) are obtained by integrating the information provided by the gyroscope and the accelerometer, the error will accumulate and be magnified over time. Accordingly, the present invention utilizes the position error correcting filters (150a, 150b, 150c) to perform the error compensation. In some embodiments of the present invention, each of the first position error correcting filter 150a, the second position error correcting filter 150b, and the third position error correcting filter 150c is a complementary filter, such as an average filter or a Kalman filter, etc. The complementary filter is to add the angle calculated by the high-frequency gyroscope and the angle calculated by the low-frequency accelerometer proportionally, thereby obtaining an angle that is less affected by the accumulated error. The calculation process of using the complementary filter to compensate the integral error should be a known technology in the relevant field, and will not be discussed and explained here.

The computing device 130 is communicatively connected to the first position error correcting filter 150a, the second position error correcting filter 150b, the third position error correcting filter 150c, the first distance sensor 120a, the second distance sensor 120b and the third distance sensor 120c, such that the computing device 130 receives the first coordinate P1 of the first position sensor 110a relative to the navigation origin, the second coordinate P2 of the second position sensor 110b relative to the navigation origin, the third coordinate P3 of the third position sensor 110c relative to the navigation origin, the first distance R1 between the first distance sensor 120a and the inner wall W of the organ, the second distance R2 between the second distance sensor 120b and the inner wall W of the organ, and the third distance R3 between the third distance sensor 120c and the inner wall W of the organ.

In some embodiments of the present invention, the computing device 130 is used to obtain a position coordinate P of the endoscope probe 140 relative to the navigation origin according to the first coordinate P1, the second coordinate P2 and the third coordinate P3. Specifically, the position coordinate P is an average value of the first coordinate P1, the second coordinate P2 and the third coordinate P3. In other words, the computing device 130 calculates an average value of the first coordinate P1, the second coordinate P2 and the third coordinate P3, thereby obtaining the position coordinate P.

In some embodiments of the present invention, the computing device 130 is used to determine whether to send a warning message according to the first distance R1, the second distance R2 and the third distance R3. Specifically, when one of the first distance R1, the second distance R2 and the third distance R3 is less than a distance threshold, the computing device 130 sends the warning message. The aforementioned distance threshold can be 1 cm, 0.5 cm, or other suitable values. In other words, the first distance R1, the second distance R2 and the third distance R3 are compared with the distance threshold, such that the system 100 for assisting endoscope tracking can send the warning message to remind the operator that the endoscope probe 140 is about to collide with the inner wall W of the organ when the distance between the inner wall W of the organ and one of the distance sensors (120a, 120b, 120c) is too close, thereby preventing the endoscope probe 140 from colliding with the inner wall of the organ so as not to cause pain to the patient and eliminate the risk of the inner wall of the organ being penetrated.

In some embodiments of the present invention, the computing device 130 is used to draw the travel path of the endoscope probe 140 within the organ according to the position coordinate P, and the computing device 130 is communicatively connected to the endoscope probe 140. Specifically, since the computing device 130 can obtain the position coordinate P of the endoscope probe 140 relative to the navigation origin at each time point after the start of the endoscope surgery, the computing device 130 can draw the travel path of the endoscope probe 140 from the initial time point (at the beginning of the endoscope surgery) to the current time point according to the position coordinate P. In some embodiments of the present invention, the system 100 for assisting endoscope tracking further includes a display screen (not shown) communicatively connected to the computing device 130. The aforementioned display screen is used to display the current intestine image captured by the endoscope probe 140 and to display the travel path of the endoscope probe 140 within the organ. In this way, the operating doctor can realize the relative spatial position of the endoscope probe 140 within the intestine, thereby assisting the doctor to accurately determine the direction or the angle for operating the endoscope probe 140 to move forward and backward so as to avoid harm to human organs.

In some embodiments of the present invention, the system 100 for assisting endoscope tracking further includes a storage device 160 communicatively connected to the computing device 130. The storage device 160 is used to store the position coordinate P corresponding to a lesion and an image (captured by the endoscope probe 140) corresponding to the lesion. Specifically, when the doctor finds the lesion during the endoscope surgery, the doctor can perform a lesion operation (for example, pressing a button on the display screen), and the computing device 130 will then store the current position coordinate P (i.e., the position coordinate P corresponding to the lesion) and the current intestine image captured by the endoscope probe 140 (i.e., the image corresponding to the lesion captured by the endoscope probe 140) to the storage device 160, thereby providing the reference basis for tracking the postoperative recovery of the lesion in the future. In other words, the doctor can utilize the information stored by storage device 160 to track the historical lesions after endoscope surgery. In detail, when tracking the postoperative recovery of the lesion in the future, the doctor can directly operate the endoscope probe 140 to move to the position coordinate P corresponding to the historically stored lesion, and then the doctor can utilize the endoscope probe 140 to capture the intestine image so as to observe the postoperative recovery of the lesion (such as the observation of the postoperative recovery after polypectomy). In other embodiments of the present invention, the storage device 160 can also be used to store the position coordinates corresponding to the endoscope probe 140 and the corresponding images at various time points during the endoscope surgery.

Figure 3:
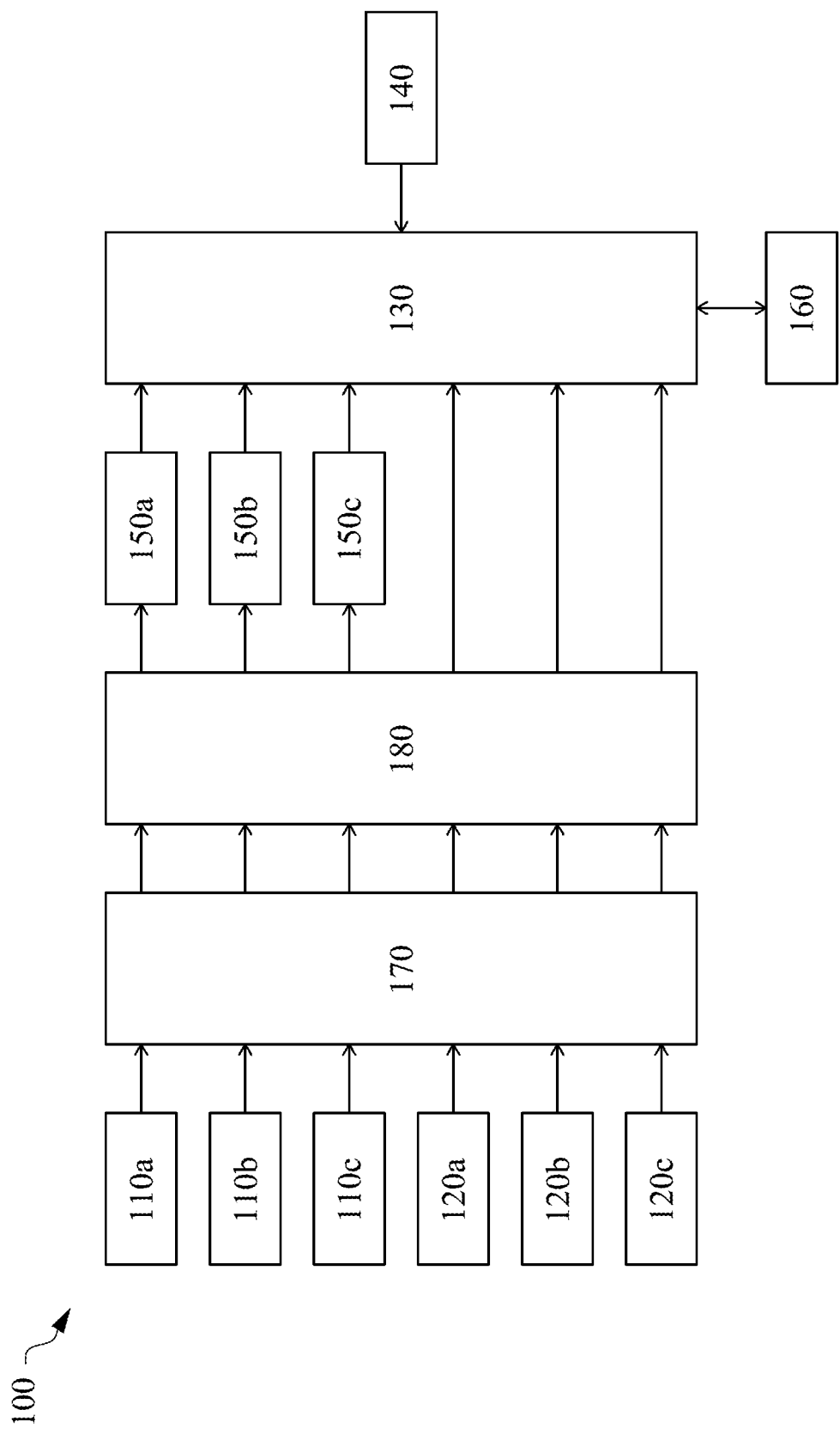
FIG. 3 illustrates a detailed block diagram of the system for assisting endoscope tracking according to some embodiments of the present invention.

FIG. 3 illustrates a detailed block diagram of the system 100 for assisting endoscope tracking according to some embodiments of the present invention. FIG. 3 is similar to FIG. 1 except that the system 100 for assisting endoscope tracking of FIG. 3 further includes a signal processing device 170 and an analog-to-digital conversion device 180.

The signal processing device 170 is communicatively connected to the position sensors (110a, 110b, 110c) and the distance sensors (120a, 120b, 120c). The signal processing device 170 is used for filtering and amplifying the sensed signals outputted by the position sensors (110a, 110b, 110c) and the distance sensors (120a, 120b, 120c). Specifically, the sensed signals outputted by the position sensors (110a, 110b, 110c) and the distance sensors (120a, 120b, 120c) may contain noise components, and therefore the signal processing device 170 is used to perform noise filtering. The manner of noise filtering can include, for example, excluding unreasonable extreme values or utilizing analog filters, etc. In addition, the sensed signals outputted by the position sensors (110a, 110b, 110c) and the distance sensors (120a, 120b, 120c) may be too small and is not suitable for subsequent calculation/operation. Thus, the signal processing device 170 is used to perform the signal amplification for amplifying the sensed signals outputted by the position sensors (110a, 110b, 110c) and the distance sensors (120a, 120b, 120c).

The analog-to-digital conversion device 180 is communicatively connected to the signal processing device 170. In some embodiments of the present invention, the analog-to-digital conversion device 180 is, for example, a microprocessor or a digital signal processor (DSP) for digital signal processing. The analog-to-digital conversion device 180 is used to perform an analog-to-digital conversion on the analog signals outputted by the position sensors (110a, 110b, 110c) and the distance sensors (120a, 120b, 120c), thereby converting the analog signals into the digital signals to facilitate the subsequent calculation/operation performed by the computing device 130.

It is noted that, in the embodiments as shown in FIGS. 1-3, the number of the position sensors (110a, 110b, 110c) and the number of the distance sensors (120a, 120b, 120c) are both 3. However, this number is merely an example and the present invention is not limited thereto. In other embodiments of the present invention, the number of the position sensors and the number of the distance sensors may both be 4 or more.

In other embodiments of the present invention, the system for assisting endoscope tracking may further include a first LED (not shown) adjacent to the first distance sensor 120a, a second LED (not shown) adjacent to the second distance sensor 120b, and a third LED (not shown) adjacent to the third distance sensor 120c. The first LED, the second LED and the third LED can be used as an auxiliary light source for the endoscope probe 140 when the endoscope probe 140 captures an image, thereby enhancing the imaging quality of the image captured by the endoscope probe 140.

It is worth mentioning that the center point of the endoscope probe 140 relative to the position coordinate P of the navigation origin is known, and the first coordinate P1, the second coordinate P2, the third coordinate P3, the first distance R1, the second distance R2 and the third distance R3 are also known, and the cross-sectional diameter of the top of the cylinder of the endoscope probe 140 is also known. Therefore, substantially, the computing device 130 can draw the shape of the intestine according to the aforementioned known conditions, such that the doctor can more accurately know the relative spatial position of the endoscope probe 140 within the intestine.

Figure 4:
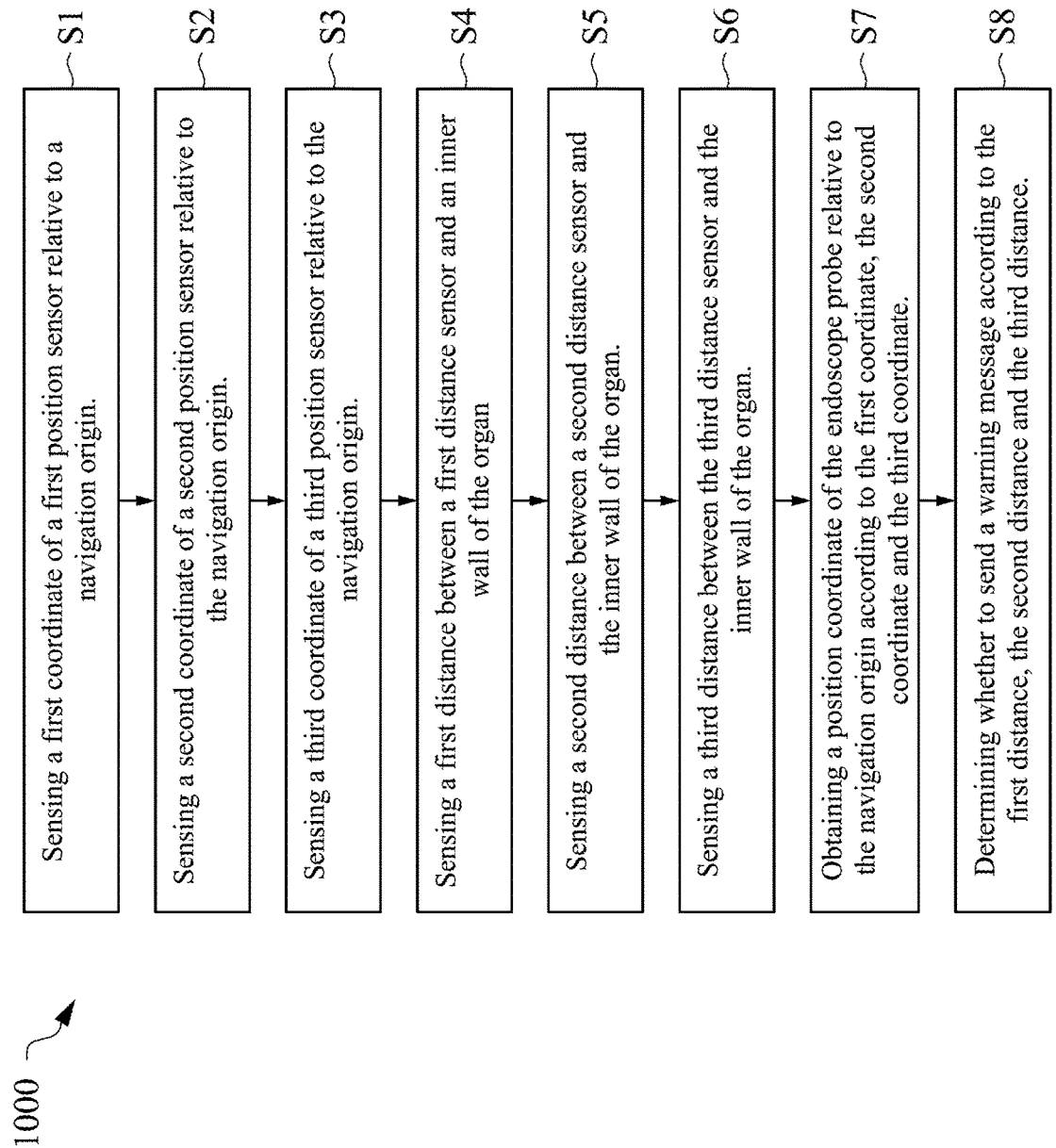
FIG. 4 illustrates a flow chart of a method for assisting endoscope tracking according to some embodiments of the present invention.

FIG. 4 illustrates a flow chart of a method 1000 for assisting endoscope tracking according to some embodiments of the present invention. The method 1000 for assisting endoscope tracking includes plural steps S1-S7. Regarding the step S1, the first position sensor 110a senses the first coordinate P1 of the first position sensor 110a relative to the navigation origin. Regarding the step S1, the second position sensor 110b senses the second coordinate P2 of the second position sensor 110b relative to the navigation origin. Regarding the step S3, the third position sensor 110c senses the third coordinate P3 of the third position sensor 110c relative to the navigation origin.

Regarding the step S4, the first distance sensor 120a adjacent to the first position sensor 110a senses the first distance R1 between the first distance sensor 120a and the inner wall W of the organ. Regarding the step S5, the second distance sensor 120b adjacent to the second position sensor 110b senses the second distance R2 between the second distance sensor 120b and the inner wall W of the organ. Regarding the step S6, the third distance sensor 120c adjacent to the third position sensor 110c senses the third distance R3 between the third distance sensor 120c and the inner wall W of the organ.

Regarding the step S7, the computing device 130 obtains the position coordinate P of the endoscope probe 140 relative to the navigation origin according to the first coordinate P1, the second coordinate P2 and the third coordinate P3. Specifically, the position coordinate P is an average value of the first coordinate P1, the second coordinate P2 and the third coordinate P3. In other words, the computing device 130 calculates an average value of the first coordinate P1, the second coordinate P2 and the third coordinate P3, thereby obtaining the position coordinate P.

Regarding the step S8, the computing device 130 determines whether to send the warning message according to the first distance R1, the second distance R2 and the third distance R3. Specifically, when one of the first distance R1, the second distance R2 and the third distance R3 is less than the distance threshold, the computing device 130 sends the warning message.

Figure 5:
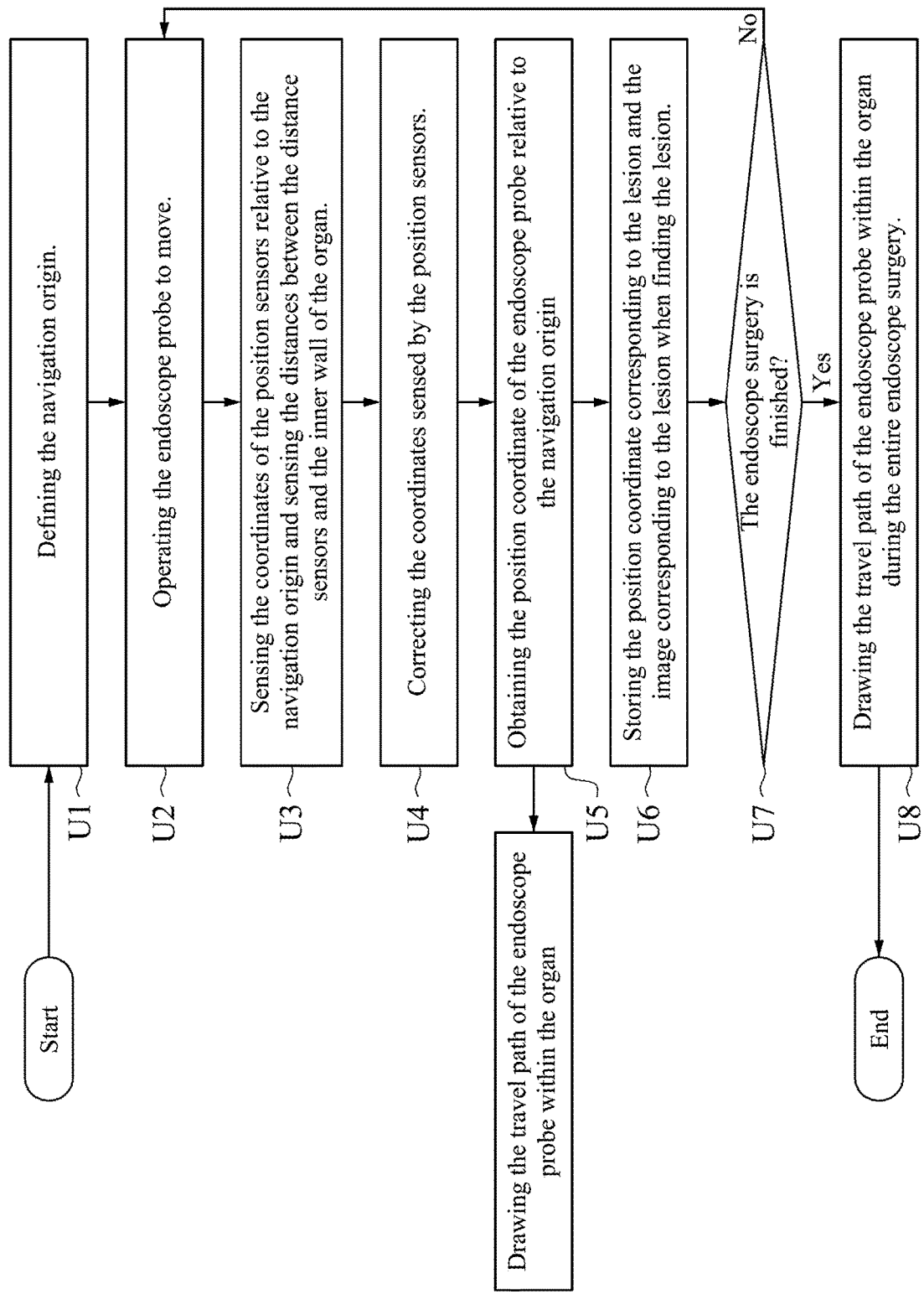
FIG. 5 illustrates a detailed flow chart of the method for assisting endoscope tracking according to some embodiments of the present invention.

FIG. 5 illustrates a detailed flow chart of the method for assisting endoscope tracking according to some embodiments of the present invention. First, at the beginning of the endoscope surgery, a starting point that the endoscope probe 140 enters the patient's body is defined as the navigation origin (step U1). Next, during the endoscope surgery, the doctor operates the endoscope probe 140 to move so as to perform the inspection (step U2).

At this time, the position sensors (110a, 110b, 110c) respectively sense its coordinates (P1, P2, P3) relative to the navigation origin, and the distance sensors (120a, 120b, 120c) respectively sense the distances (R1, R2, R3) between the distance sensors (120a, 120b, 120c) and the inner wall W of the organ (step U3). Next, the position error correcting filters (150a, 150b, 150c) respectively correct the coordinates (P1, P2, P3) sensed by the position sensors (110a, 110b, 110c) (step U4).

Next, the computing device 130 obtains the position coordinate P of the endoscope probe 140 relative to the navigation origin according to the first coordinate P1, the second coordinate P2 and the third coordinate P3 (step U5), thereby drawing the travel path of the endoscope probe 140 within the organ.

Next, when the doctor finds the lesion during the endoscope surgery, the doctor can store the position coordinate P corresponding to the lesion and the image (captured by the endoscope probe 140) corresponding to the lesion, thereby providing the reference basis for tracking the postoperative recovery of the lesion in the future (step U6).

Next, determining whether the endoscope surgery is finished (step U7). If the endoscope surgery has not ended, go back to step U2. If the endoscope surgery has ended, the computing device 130 draws the travel path of the endoscope probe 140 within the organ during the entire endoscope surgery (step U8), and the process is ended.

From the above description, the present invention provides the system for assisting endoscope tracking and the method for assisting endoscope tracking. The present invention utilizes three position sensors to obtain the position coordinates of the endoscope probe relative to the navigation origin, such that the travel path of the endoscope probe within the organ can be drawn. The aforementioned travel path can assist the doctor to accurately determine the direction or the angle for operating the endoscope probe to move forward and backward so as to avoid harm to human organs. In addition, the present invention utilizes three distance sensors to obtain the distances between the three distance sensors and the inner wall of the organ, such that the warning message is sent when the endoscope probe is about to collide with the inner wall of the organ so as not to cause pain to the patient and eliminate the risk of the inner wall of the organ being penetrated.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A system for assisting endoscope tracking is disclosed, wherein the system is used to track a travel path of an endoscope probe within an organ, wherein the system comprises:
    a first position sensor configured to sense a first coordinate of the first position sensor relative to a navigation origin;
    a second position sensor configured to sense a second coordinate of the second position sensor relative to the navigation origin;
    a third position sensor configured to sense a third coordinate of the third position sensor relative to the navigation origin, wherein the first position sensor, the second position sensor and the third position sensor are surrounding the endoscope probe;
    a first distance sensor adjacent to the first position sensor, wherein the first distance sensor is configured to sense a first distance between the first distance sensor and an inner wall of the organ;
    a second distance sensor adjacent to the second position sensor, wherein the second distance sensor is configured to sense a second distance between the second distance sensor and the inner wall of the organ;
    a third distance sensor adjacent to the third position sensor, wherein the third distance sensor is configured to sense a third distance between the third distance sensor and the inner wall of the organ; and
    a computing device configured to obtain a position coordinate of the endoscope probe relative to the navigation origin according to the first coordinate, the second coordinate and the third coordinate;
    wherein the computing device is further configured to determine whether to send a warning message according to the first distance, the second distance and the third distance.

2. The system of claim 1, wherein each of the first position sensor, the second position sensor and the third position sensor is a MEMS inertial sensing device composed of a gyroscope and an accelerometer.

3. The system of claim 1, wherein each of the first distance sensor, the second distance sensor and the third distance sensor is an infrared distance sensor, wherein a detectable range of the infrared distance sensor is 0 to 6 cm.

4. The system of claim 1, wherein the position coordinate is an average value of the first coordinate, the second coordinate and the third coordinate, wherein the computing device draws the travel path of the endoscope probe within the organ according to the position coordinate.

5. The system of claim 1, wherein when one of the first distance, the second distance and the third distance is less than a distance threshold, the computing device sends the warning message.

6. The system of claim 1, further comprising:
 a first position error correcting filter configured to correct the first coordinate sensed by the first position sensor;
 a second position error correcting filter configured to correct the second coordinate sensed by the second position sensor; and
 a third position error correcting filter configured to correct the third coordinate sensed by the third position sensor.

7. The system of claim 6, wherein each of the first position error correcting filter, the second position error correcting filter and the third position error correcting filter is a complementary filter.

8. The system of claim 1, further comprising:
 a storage device configured to store the position coordinate corresponding to a lesion and an image corresponding to the lesion, wherein the image is captured by a camera part of the endoscope probe.

9. A method for assisting endoscope tracking is disclosed, wherein the method is used to track a travel path of an endoscope probe within an organ, wherein the method comprises:
 sensing a first coordinate of a first position sensor relative to a navigation origin;
 sensing a second coordinate of a second position sensor relative to the navigation origin;
 sensing a third coordinate of a third position sensor relative to the navigation origin, wherein the first position sensor, the second position sensor and the third position sensor are surrounding the endoscope probe;
 sensing a first distance between a first distance sensor and an inner wall of the organ, wherein the first distance sensor is adjacent to the first position sensor;
 sensing a second distance between a second distance sensor and the inner wall of the organ, wherein the second distance sensor is adjacent to the second position sensor;
 sensing a third distance between a third distance sensor and the inner wall of the organ, wherein the third distance sensor is adjacent to the third position sensor;
 obtaining a position coordinate of the endoscope probe relative to the navigation origin according to the first coordinate, the second coordinate and the third coordinate; and
 determining whether to send a warning message according to the first distance, the second distance and the third distance.

10. The method of claim 9, wherein each of the first position sensor, the second position sensor and the third position sensor is a MEMS inertial sensing device composed of a gyroscope and an accelerometer.

11. The method of claim 9, wherein each of the first distance sensor, the second distance sensor and the third distance sensor is an infrared distance sensor, wherein a detectable range of the infrared distance sensor is 0 to 6 cm.

12. The method of claim 9, further comprising:
 drawing the travel path of the endoscope probe within the organ according to the position coordinate;
 wherein the position coordinate is an average value of the first coordinate, the second coordinate and the third coordinate.

13. The method of claim 9, further comprising:
 sending the warning message when one of the first distance, the second distance and the third distance is less than a distance threshold.

14. The method of claim 9, further comprising:
 correcting the first coordinate sensed by the first position sensor by a first position error correcting filter;
 correcting the second coordinate sensed by the second position sensor by a second position error correcting filter; and
 correcting the third coordinate sensed by the third position sensor by a third position error correcting filter.

15. The method of claim 14, wherein each of the first position error correcting filter, the second position error correcting filter and the third position error correcting filter is a complementary filter.

16. The method of claim 9, further comprising:
 capturing an image corresponding to a lesion by a camera part of the endoscope probe and storing the position coordinate corresponding to the lesion and the image corresponding to the lesion.

\* \* \* \* \*